United States Patent
Flexman et al.

(10) Patent No.: US 11,123,031 B2
(45) Date of Patent: Sep. 21, 2021

(54) AUGMENTED REALITY FOR RADIATION DOSE MONITORING

(71) Applicant: KONINKLIJKE PHILIPS N.V., Eindhoven (NL)

(72) Inventors: Molly Lara Flexman, Melrose, MA (US); Ashish Panse, Burlington, MA (US); Alalao Ayman, Cambridge, MA (US); Christopher Martel, Andover, MA (US); Marcin Arkadiusz Balicki, Cambridge, MA (US)

(73) Assignee: KONINKLIKE PHILIPS N.V., Eindhoven (NL)

( * ) Notice: Subject to any disclaimer, the term of this patent is extended or adjusted under 35 U.S.C. 154(b) by 14 days.

(21) Appl. No.: 16/478,137

(22) PCT Filed: Jan. 16, 2018

(86) PCT No.: PCT/EP2018/050929
§ 371 (c)(1),
(2) Date: Jul. 16, 2019

(87) PCT Pub. No.: WO2018/134172
PCT Pub. Date: Jul. 26, 2018

(65) Prior Publication Data
US 2019/0365339 A1      Dec. 5, 2019

Related U.S. Application Data

(60) Provisional application No. 62/447,212, filed on Jan. 17, 2017.

(51) Int. Cl.
*G01J 1/42*          (2006.01)
*A61B 6/00*         (2006.01)
(Continued)

(52) U.S. Cl.
CPC .............. *A61B 6/465* (2013.01); *A61B 6/107* (2013.01); *A61B 6/4441* (2013.01); *G01T 1/02* (2013.01);
(Continued)

(58) Field of Classification Search
CPC ....... A61B 6/465; A61B 6/107; A61B 6/4441; A61B 2090/365; G16H 20/40; G16H 40/63; G01T 1/02; G06T 13/80; G06T 2210/41
See application file for complete search history.

(56) References Cited

U.S. PATENT DOCUMENTS

2013/0062527 A1*   3/2013   Hyde ...................... G01T 1/161
                                                                              250/366
2017/0091387 A1*   3/2017   Kuusela ................. G16H 50/30

FOREIGN PATENT DOCUMENTS

EP         2982415 A1    2/2016
WO    2008104915 A2    9/2008

OTHER PUBLICATIONS

PCT/EP2018/050929 ISR and Written Opinion, dated Apr. 23 2018, 12 Page Document.

(Continued)

*Primary Examiner* — Kiho Kim

(57) ABSTRACT

A system (300) for radiation dose monitoring in a medical environment (305) includes an imaging device (310) for directing radiation (312) onto a patient (315) and a radiation dose measuring device (325) for measuring a radiation dose of at least one medical personnel (320) within the medical environment (305). The system further includes a processor (327) for receiving radiation dose information of the patient or of the at least one medical personnel, and for rendering, in real-time, a virtual object (401) associated with each radiation dose measuring device (325), the virtual object (401) representing radiation dose information. The system (Continued)

can further include a display (340) for displaying distribution of radiation (505) in the medical environment (305).

27 Claims, 7 Drawing Sheets

(51) Int. Cl.
  *G16H 20/40* (2018.01)
  *G16H 40/63* (2018.01)
  *A61B 6/10* (2006.01)
  *G01T 1/02* (2006.01)
  *G06T 13/80* (2011.01)
(52) U.S. Cl.
  CPC ............. *G06T 13/80* (2013.01); *G16H 20/40* (2018.01); *G16H 40/63* (2018.01); *G06T 2210/41* (2013.01)

(56) References Cited

OTHER PUBLICATIONS

Tu Mai: "The Use FO a Real-Time Displayed Measuring System Fior X-Rays"; Master Degree Thesis in Radiation Physics, University of Gothenburg, Gothenburg, Sweden, Jan. 2011, 35 Pages.

\* cited by examiner

AUGMENTED REALITY FOR RADIATION DOSE MONITORING

CROSS-REFERENCE TO PRIOR APPLICATIONS

This application is the U.S. National Phase application under 35 U.S.C. § 371 of International Application No. PCT/EP2018/050929, filed on Jan. 16, 2018, which claims the benefit of U.S. Provisional Patent Application No. US62/447,212, filed on Jan. 17, 2017. These applications are hereby incorporated by reference herein.

BACKGROUND

Technical Field

This disclosure relates to augmented reality systems and methods, and, more particularly, to using augmented reality for radiation dose monitoring in an operating room environment.

Description of the Related Art

A hybrid operating room (OR) and catheterization laboratory (cathlab) rely on ionizing radiation to perform 2D and 3D intraoperative imaging. The ALARA (as low as reasonably achievable) concept aims to reduce dose to the patient and staff in the operator room. There are many mechanisms to reduce dose, including lead aprons, lead shields, and, wedges, and staff awareness. New techniques for monitoring dose are available including real-time dosimeter badges for staff, and real-time patient skin dose monitoring.

Augmented reality generally refers to a situation when a live image stream is supplemented with additional computer-generated information. The live image stream can be provided using the eye, cameras, smart phones, tablets, etc. This image stream is augmented by a display to the user. The augmented display can be conveyed to the user via glasses, contact lenses, projections or on a live image stream device (e.g., smart phone, tablet, etc.).

SUMMARY

In accordance with the present principles, a system for radiation dose monitoring in a medical environment includes an imaging device for directing radiation onto a patient and a radiation dose measuring device for measuring a radiation dose of at least one medical personnel within the medical environment. The system further includes a processor for receiving radiation dose information of the patient or of the at least one medical personnel, and for rendering, in real-time, a virtual object associated with each radiation dose measuring device, the virtual object representing radiation dose information.

A system includes an imaging device for directing radiation onto a patient, a radiation dose measuring device for measuring a radiation dose of at least one medical personnel within the medical environment and a processor for receiving at least radiation dose information of the patient or of the at least one medical personnel, geometry information from the imaging device, radiation information from the imaging device, and topology information related to the medical environment. The system further includes a display for displaying distribution of radiation in the medical environment.

A method includes directing radiation onto a patient by an imaging device, measuring a radiation dose of at least one medical personnel within the medical environment, receiving, by a processor, radiation dose information of the patient or of the at least one medical personnel, and rendering, in real-time, a virtual object associated with each radiation dose measuring device, the virtual object representing radiation dose information.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
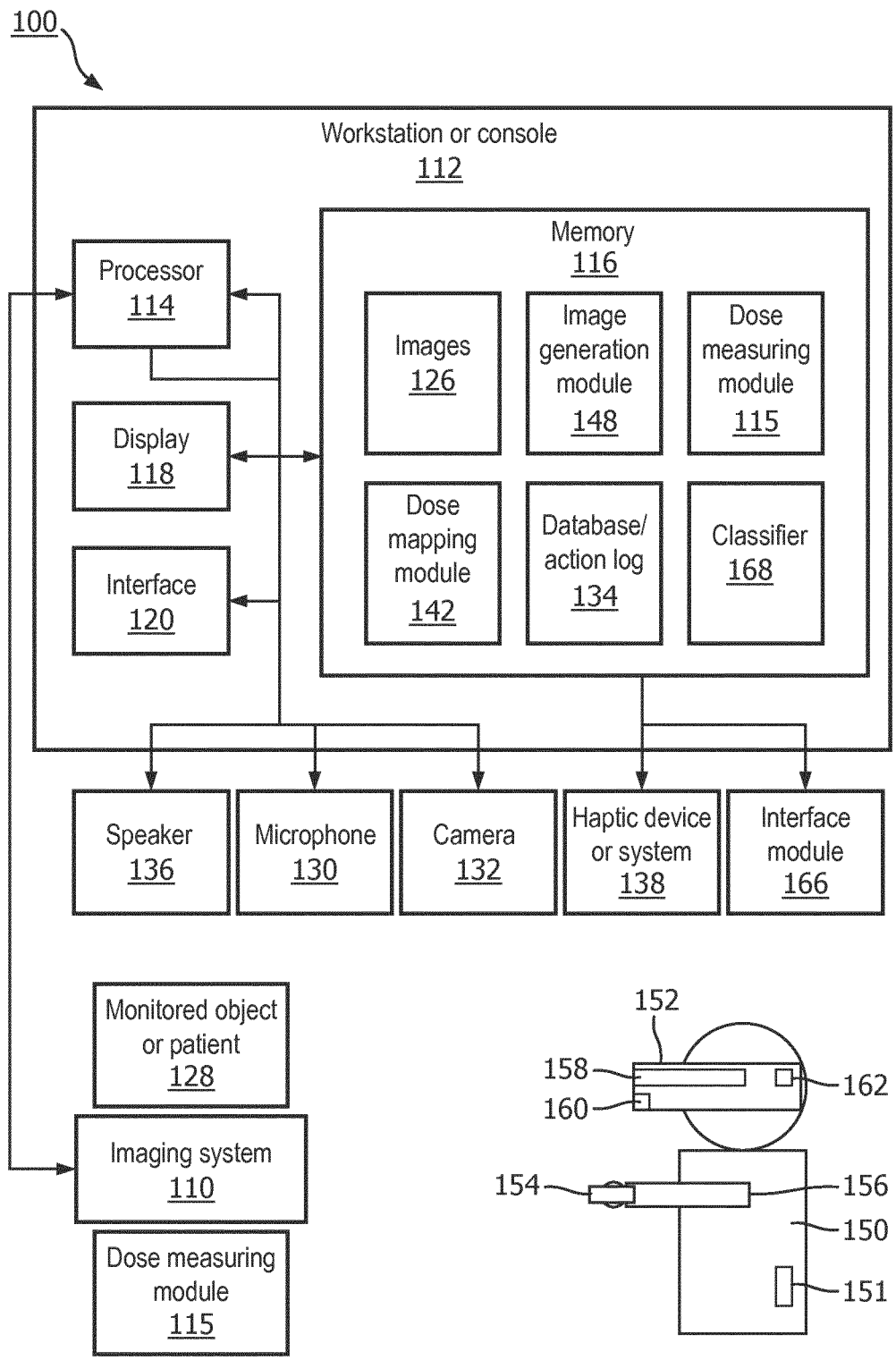
FIG. 1 is a block/flow diagram showing a dose measuring and mapping system, in accordance with one embodiment.

In accordance with the present principles, systems, devices and methods are provided for augmented reality for radiation dose monitoring in an operating room (OR) environment. Embodiments described herein provide radiation dose measuring and mapping capabilities with the aid of augmented reality (AR) data/information associated with medical procedures or other work environment activities, e.g., in a manufacturing environment or the like. In particularly useful embodiments, a head mounted display is employed, which can include display glasses, display lenses, head mounted display scenes, virtual reality fixtures with tablets, smart phones, etc.

In one embodiment, patient dose information is computed pre-operatively or intra-operatively and can raise awareness for the operator during the medical procedure. The patient dose map can be overlayed on the patient by using augmented reality. In many cases, the operator can adjust the c-arm position or use wedges to help reduce the radiation dose to a skin region of a patient that has already received a high radiation dose. The augmented reality overlay can be supplemented with a notification or warning when the c-arm position is leading to additional radiation dose to a region that is already above a certain threshold. It could also suggest an alternate c-arm position to avoid that region. In addition to the patient dose map overlay, the current c-arm dose distribution can be overlayed to highlight where the dose will be applied, especially with respect to the patient dose map.

In one embodiment, the x-ray beams scatter as they interact with various materials such as the table, the patient, instruments, etc. The scattered beams are what cause the majority of the dose to the medical staff/personnel in the operating room (OR). Since the scattering events are complex, the medical staff/personnel in the OR are often not aware of how much radiation they are receiving at any given time. If they are aware that they are receiving a lot of radiation then they can make subtle changes to their workflow (e.g., a nurse shifting his/her position in the room slightly or an operator remembering to use a lower radiation level when the higher level is not clinically necessary). The use of augmented reality can help to communicate the information about radiation in the room.

There are multiple ways in which this can be useful. In one embodiment, dose avatars are presented. In another embodiment, a dose dashboard is introduced in the OR. In yet another embodiment, room radiation topology can be displayed to indicate regions within the OR with high levels, medium levels, and/or low levels of radiation exposure. The system can use any dosimeter readings that are present in the room, combined with the geometry and radiation information from the c-arm, plus the camera view of the patient and room setup to model and then overlay on the view the distribution of radiation in the room. The distribution of radiation in the room can be shown in many ways, such as (i) small particles that exit the source and follow a trajectory, (ii) an overlay on any surfaces in the room that is color-coded by the amount of radiation encountering on that surface, and (iii) an overlay of low-radiation locations to stand on (floor overlay, e.g., footprints) or below (ceiling overlay) to avoid radiation exposure. The location suggestions can be unique per staff member to avoid crowding, and minimize traffic, and distance travelled. The dose radiation system can be used to display cumulative historical information, current radiation, and expected radiation for upcoming x-ray use and the system could be used for training and simulation. The dose radiation system could alternatively be turned on occasionally during the procedure by the operator.

In one embodiment, a radiation proximity warning can be provided to the medical staff/personnel, where the dose radiation system estimates the radiation intensity and geometry immediately prior to taking an x-ray image(s). Each staff member's location relative to expected radiation field is considered along with their current radiation exposure and estimated additional exposure from the planned x-ray. The staff member that has potential of exceeding the radiation exposure limit for the planned x-ray is provided information by (i) alerts, such as audio, text message, screen flash, etc., (ii) visual display of the areas of the room that are a no-go for that staff member, e.g., "painted" in a distinct color, e.g., red, and (iii) the X-ray operator is alerted of the potential over-exposure and the staff in person is highlighted on operator's display and has to override the warning by a gesture, such as virtually clicking on the staff's avatar.

In another embodiment, the virtual representation of the dose can be placed relative to a staff member/patient/room location by a variety of methods, such as, but not limited to, manual placement, detection of a marker on the person/location/equipment/dosimeter badge, facial recognition, detection of a person's body outline (patient), and/or position in the room. In an alternative embodiment, the dose can be shown/presented as a dashboard in the user's/wearer's view. One skilled in the art can contemplate a number of different ways to display/present the virtual representation of the dose.

As used herein, the augmented reality (AR) based dose radiation system generally may be referred to as an AR supported and/or an AR enhanced system. The AR based user dose radiation system may be helpful in environments that include users (assisting staff) that treat a patient. With the help of advanced AR technology (e.g., adding computer vision and object recognition to a real-life representation) the information about the surrounding real world of the user becomes interactive and digitally manipulable. Artificial information about the environment and its objects can be overlaid on the medical environment. This may have the advantage that an interactive instructive manual can be provided that may be further enhanced in that corrective user feedback may be presented. Generally, positive feedback (i.e., a procedure or a sub-step thereof has been successfully accomplished) may be provided.

It should be understood that the present invention will be described in terms of medical instruments; however, the teachings of the present invention are much broader and are applicable to any acoustic instruments. In some embodiments, the present principles are employed in tracking or analyzing instruments in complex biological or mechanical systems. In particular, the present principles are applicable to internal and/or external tracking procedures of biological systems and procedures in all areas of the body such as the lungs, gastro-intestinal tract, excretory organs, blood vessels, etc. The functional elements depicted in the FIGS. may be implemented in various combinations of hardware and software and provide functions which may be combined in a single element or multiple functional elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a dose measuring and mapping system is illustratively shown in accordance with one embodiment.

Figure 5:
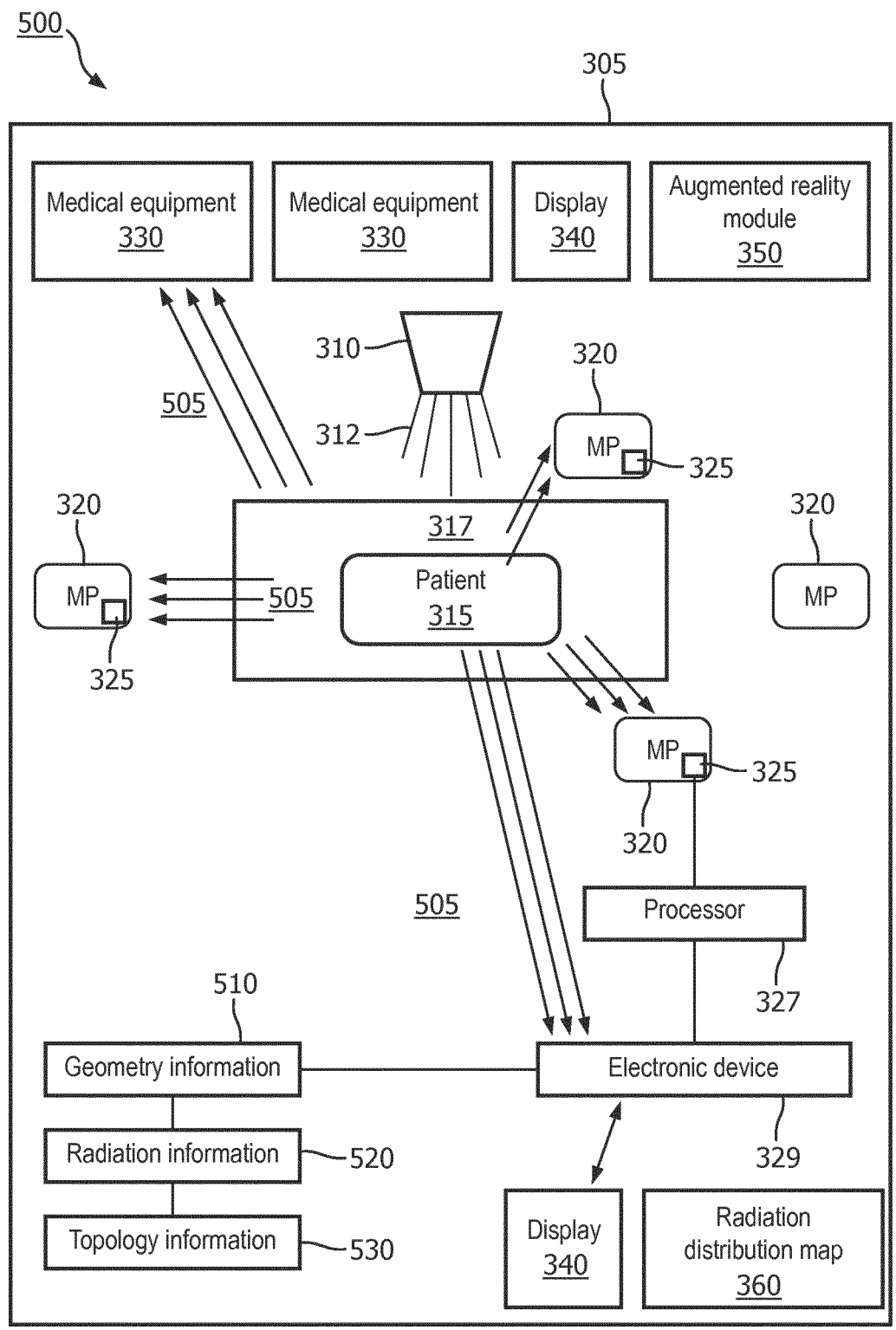
FIG. 5 is a block/flow diagram showing an operating room environment capable of displaying a radiation distribution map, in accordance with one embodiment.

System 100 can include a collection of modules that can be integrated into a workstation 112, which can include a single console or can include separate modules connected together. Workstation 112 preferably includes one or more processors 114 and memory 116 for storing programs and applications. Memory 116 may store a dose measurement module 115 configured to interpret feedback from one or more inputs to provide feedback to a radiation distribution map 360 (FIG. 5). Alternatively, the dose measurement module 115 can be positioned outside the workstation 112.

The dose measurement module 115 employs historic data stored in a database or action log 134. The action log 134 stores use activities during an augmented reality session. The action log 134 stores event data (e.g., temporal data, counts (number of times an action (e.g., an event or procedure step) is performed), the type of action, the source or equipment registering the action, the magnitude or characteristics of the action, the identity of the user, etc. It should be understood that the types of inputs can vary widely depending on the applications, the equipment, the configuration of the environment, etc. The data entered into the action log 134 can be classified based on the input type or source; however, in a larger setting with a large number of inputs, a classifier 168 may be employed. The classifier 168 receives the inputs and tags the inputs for ease of use for model comparison and database storage.

For example, in one embodiment, an augmented reality user 150 employs a head-mounted device 152. The device 152 can include any suitable head-mounted virtual reality system, e.g., GOOGLE GLASS™, HOLOLENS™, MAGIC LEAP™, VUSIX™), and can include two or three-dimensional capability. The device 152 provides visual feedback in the form of overlays or other images or indicators to provide dose radiation data/information to the user 150 during a procedure. The device 152 can also include a camera 158 or other sensor device or devices to provide feedback as to a current action or activity of the user 150. The augmented reality user 150 can also have a dosimeter badge 151 attached thereto.

In addition, data can be collected from a user who is using augmented reality that may include a plurality of sources. In one example, a camera feed of a user view and/or other view within the environment can be provided by camera 158 and by a remote camera 132. Eye tracking and/or head tracking can be provided by retina tracking using the capabilities of the head-mounted device or using a retinal scanner 160 and/or one or more motion tracking devices 162, e.g., accelerometers, infrared tracking, optical fiber tracking, electromagnetic (EM) tracking) or other tracking mechanism(s)). In another embodiment, voice commands can be stored, modeled and employed for aiding in the monitoring and mapping of dose radiation. A microphone 130 can be employed for recording the verbal commands and a speaker 136 can be employed for providing to the user regarding dose measurements within the medical environment.

In another embodiment, hand gestures or body configuration can be determined using camera 132 and/or a sensor or sensors 154 provided on the user 150. For example, a sensor 154 can be placed on an arm or hand 156 of the user 150 to track its motion. Any number of technologies as described here can be employed for gesture tracking. Additionally, the dosimeter badge 151 can be attached to the user 150 to track dose.

The information received from one or more sources can be combined with other available data during the procedure. The database 134 or classifier 168 can organize the data into a procedural sequence of events. This sequence of events can be associated with a procedure (and other indicia, such as user, procedure variation types, etc.) and called up when a familiar action sequence is detected to monitor dose radiation in augmented reality through the rest of the procedure or to change settings as needed or desired during the procedure.

By way of example, the system 100 can include a haptic device 138 relating to the perception and manipulation of objects using the senses of touch and proprioception.

An imaging system 110 can include an x-ray system, ultrasound system, computed tomography system, magnetic resonance, etc. In one embodiment, the imaging system 110 include a C-arm x-ray system. The procedure may call for a user 150 to focus their eye on a display 118 for an amount of the time when x-ray images 126 are being gathered, or the user 150 may change their focus a number of times between the display 118 and an interface module 166, which is employed for controlling x-ray image modes, x-ray exposure conditions, view settings, etc. The system 100 can sense the gaze of the user 150 on display 118, record the display imaging mode from the display 118 and employ other data such as hand motion, settings of the interface module 166, etc. to associate these activities with a given procedure. This data is classified and associated using the database 134 and/or the classifier 168.

In one embodiment, workstation 112 includes an image generation module 148 configured to receive feedback from one or more sources and to provide text displays, graphic displays, intensity changes, etc. in the augmented reality display 152. The augmented reality display 152 can employ overlays or markers or other rendering to provide dose radiation measuring and mapping capabilities/functions/operations.

In particularly useful embodiments, the system 100 can suggest when there is an opportunity to reduce dose to the patient and/or staff by selecting a different protocol, fluoro flavour, c-arm position, or a different location for people standing in the room. The system 100 can bring up protocols, imaging data, device information, camera feeds, etc. at appropriate times based on past cases that were similar.

The present embodiments apply to the use of augmented reality in a cathlab or hybrid operating room to measure and map radiation dose. The present embodiments are also applicable to, for example, mobile x-ray, ultrasound, CT, etc.

Workstation 112 includes the display 118 for viewing internal images of a subject (patient) 128. Display 118 may also permit a user to interact with the workstation 112 and its components and functions, or any other element within the system 100. This is further facilitated by an interface 120 which may include a keyboard, mouse, a joystick, a haptic device 138, or any other peripheral or control to permit user feedback from and interaction with the workstation 112.

Figure 2:
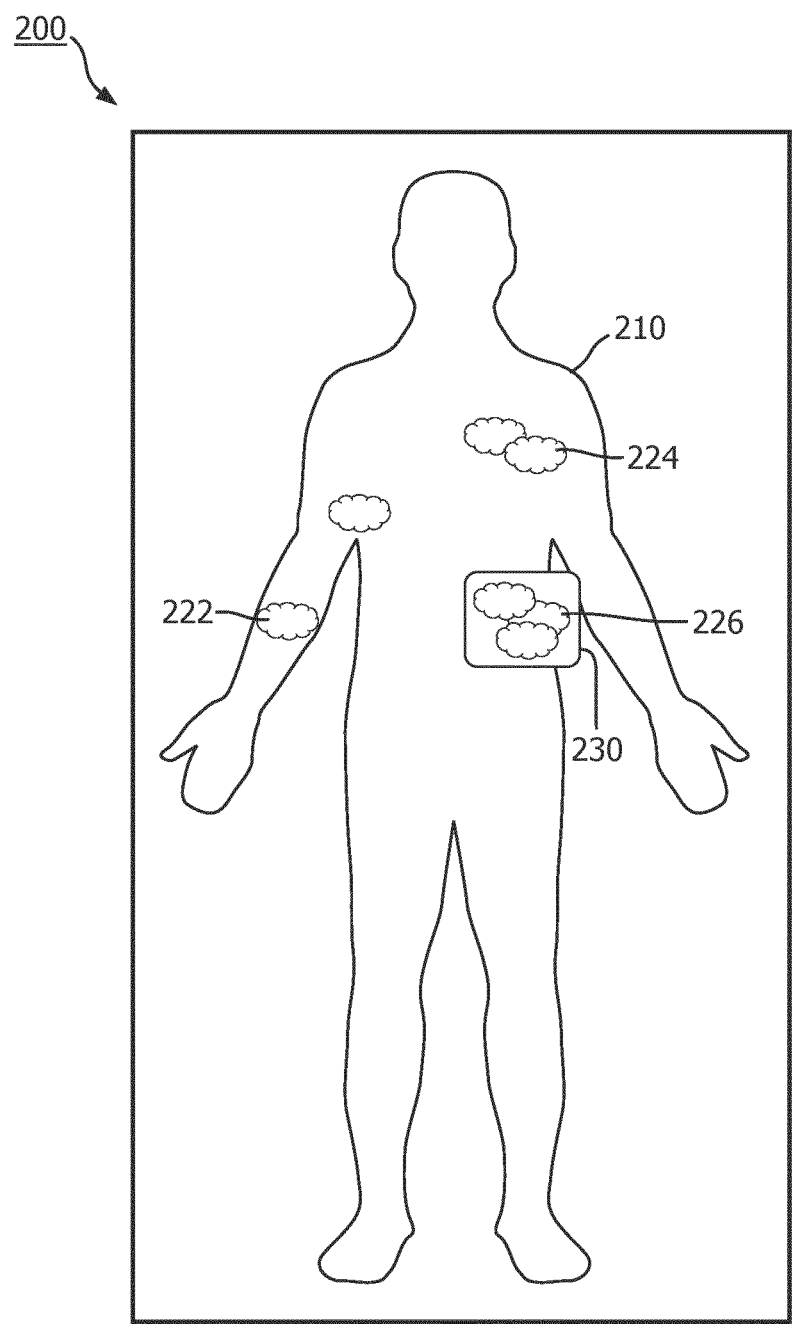
FIG. 2 is a patient dose map with an augmented reality (AR) overlay, in accordance with one embodiment.

FIG. 2 is a patient dose map with an augmented reality (AR) overlay, in accordance with one embodiment.

The patient dose display 200 depicts a patient 210 and a plurality of dose maps at several different spots or points or regions or areas on the patient's 210 body. A first dose map 222 can be, e.g., monitored on an arm of the patient 210. A second dose map 224 can be, e.g., monitored on a shoulder of the patient 210. A third dose map 226 can be, e.g., monitored on an abdominal region of the patient 210. An augmented reality overlay can be positioned over all the dose maps 222, 224, 226. In addition, the current c-arm dose distribution overlay 230 can be overlayed to highlight where the dose will be applied.

Augmented reality generally refers to when a live image stream is supplemented with additional computer-generated information. The live image stream can be via the eye, cameras, smart phones, tables, etc. This image stream is augmented via display to the user that can be done via glasses, contact lenses, projections or on the live image stream device itself (smart phone, tablet, etc.). This invention can be applied to any implementation of augmented reality.

Generally, augmented reality devices may be referred to as wearable devices, and may involve hand-held devices, optical head-mounted displays, etc. Augmented reality (AR) may be referred to as a live direct or indirect view of a physical, real-world environment whose elements may be augmented (or, in other words, supplemented) by computer-generated sensory input such as sound, video, graphics or GPS data. Put differently, layers containing artificial information may be superimposed to a representation of layers containing real-world information. Generally, augmented information may be visually presented to a user that observes a real-life scene, either directly or in a mediate way. However, also audio information, speech information, tactile information, etc. may be overlaid on a real-world perception in an augmented reality environment.

In a general sense, augmented reality may relate to a more general concept that may be referred to as mediated reality. Mediated reality generally involves that a representation or view of reality is modified by computing devices. Modifications in this context may involve emphasizing, diminishing, or even hiding real-world information elements. Augmented reality devices may therefore influence, preferably enhance, a user's current perception of reality. Generally, augmented reality involves real-time or nearly real-time augmentation or superimposition of information.

A medical procedure is a course of action intended to achieve a result in the care of persons that may potentially have health issues or even health problems. Generally, medical procedures may involve medical tests, medical monitoring, medical treatment, medical therapy, rehabilitation measures, etc. Medical tests are generally conducted with the intention of determining, measuring or diagnosing a patient condition or parameter. According to the exemplary embodiments of the present disclosure, augmented reality can be used in operating room (OR) or medical environments to monitor and measure and map radiation dose emitted by one or more imaging devices, such as an X-ray device.

In FIG. 2, patient dose information is computed pre-operatively or intra-operatively and can raise awareness for the operator during the procedure. The patient dose maps 222, 224, 226 can be overlayed on the patient 210 by using augmented reality. In many cases, the operator can adjust the c-arm position or use wedges to help reduce the dose to a skin region that has already received a high radiation dose. The augmented reality overlay can be supplemented with a notification or warning when the c-arm position is leading to additional dose to a region that is already above a certain threshold. It could also suggest an alternate c-arm position to avoid that region. In addition to the patient dose map overlay, the current c-arm dose distribution overlay 230 can be overlayed to highlight where the dose will be applied.

Figure 3:
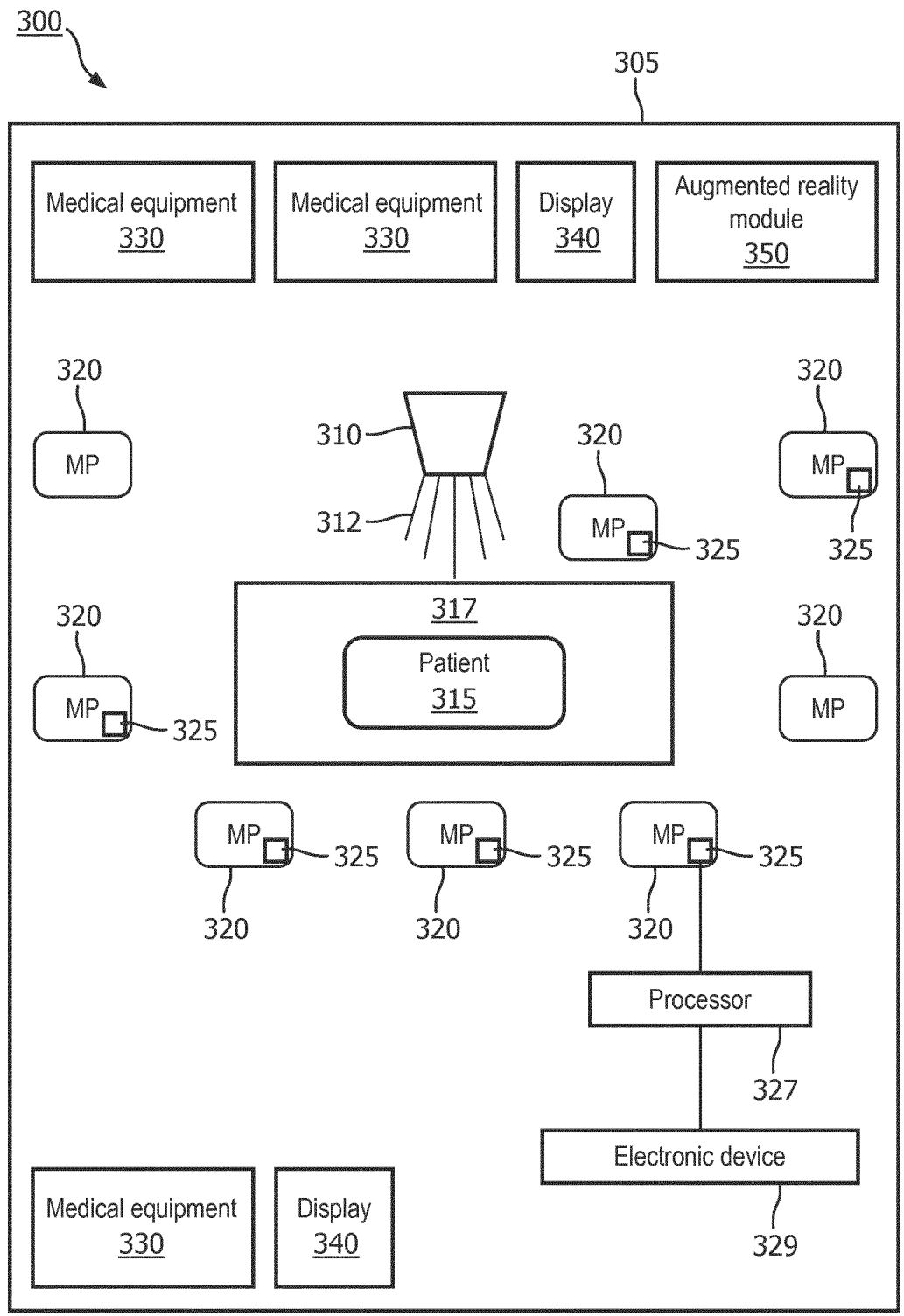
FIG. 3 is a block/flow diagram showing an operating room environment having augmented reality capabilities, in accordance with one embodiment.

FIG. 3 is a block/flow diagram showing an operating room environment having augmented reality capabilities, in accordance with one embodiment.

The system 300 depicts an operating room (OR) 305 or medical environment 305 including an imaging device 310 that emits rays or beams or radiation 312. In one example, the imaging device 310 can be an x-ray device. The radiation 312 can be ionizing radiation. The radiation 312 is directed toward a patient 315 laying on a medical table 317. A plurality of medical personnel 320 can be working in the OR 305. The medical personnel 320 can include, for example, physicians, nurses, and other medical assistants. The medical personnel 320 can have a radiation dose measuring device 325 attached thereon, in addition to the dosimeter badge 151 (FIG. 1). It is noted that all medical personnel 320 have a dosimeter badge on their person. However, not all medical personnel 320 necessarily have a radiation dose measuring device 325 attached thereon.

At least one medical personnel 320 can have a wearable electronic device 329. The wearable electronic device 329 can be, e.g., a head-mounted device 152 described in FIG. 1. The wearable electronic device 329 can include one or more processors 327. It is contemplated that one or more medical personnel 320 can wear a wearable electronic device 329.

The OR 305 can include a plurality of medical equipment 330, as well as a plurality of monitors or displays 340. All this equipment can be in bidirectional communication with an augmented reality module 350.

The AR device 350 may be arranged as a wearable computing device 329, e.g. a portable device, hand held device, head mounted device, etc. Generally, the AR device 350 may comprise a display that is arranged to overlay information on a real-life representation. The real-life representation may be directly or indirectly perceivable for the user or medical personnel 320. An indirectly presented real-life image may be captured and (more or less) instantly represented at a display 340. Preferably, a respective sensor (imaging unit, or, camera) and the display unit are (physically or virtually) aligned such that the representation of the real-life image basically matches the "real" real-life environment when the user looks at the display of the device.

In the alternative, the real-life environment that is directly perceivable to the user's eye may be enriched or enhanced by supplemental information. This may involve that potential display elements provided at the display unit are basically transparent or translucent. Such a display unit may be arranged as a so-called micro display which includes means for projecting image date in a user's field of view. As indicated above, the user may be the patient himself/herself or another person that helps and/or treats the patient in the course of the medical procedure. Hence, in some embodiments, the AR device is worn by the patient. In some embodiments, the AR device is held or worn by another person. The AR device may be held or worn by someone outside the room or even in a remote location.

Figure 4A:
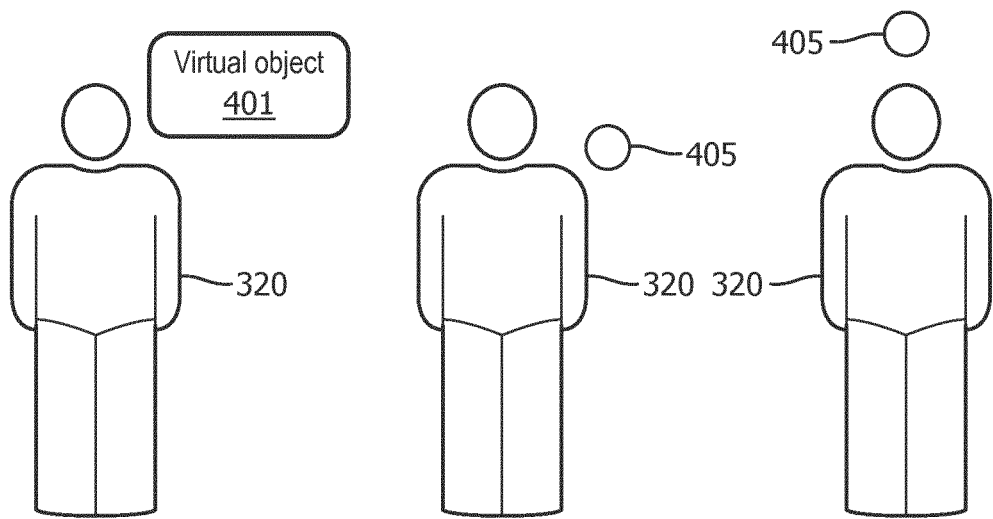
FIG. 4A is a diagram of medical personnel having a virtual object associated therewith, such as a sphere, in accordance with one embodiment.

FIG. 4A is a diagram of medical personnel having a virtual object associated therewith, such as a sphere, in accordance with one embodiment.

A medical personnel 320 can have a virtual object 401 associated therewith (leftmost user). In one example, the virtual object 401 can be a sphere 405. The sphere 405 can be positioned on or adjacent the upper portion (e.g., shoulder or arm) of the medical personnel 320 (middle user). Alternatively, the sphere 405 can be positioned over a head or in a region above the medical personnel 320 (rightmost user). One skilled in the art can contemplate positioning the virtual object 401 or sphere 405 on any location in the vicinity or on the medical personnel 320.

Figure 4B:
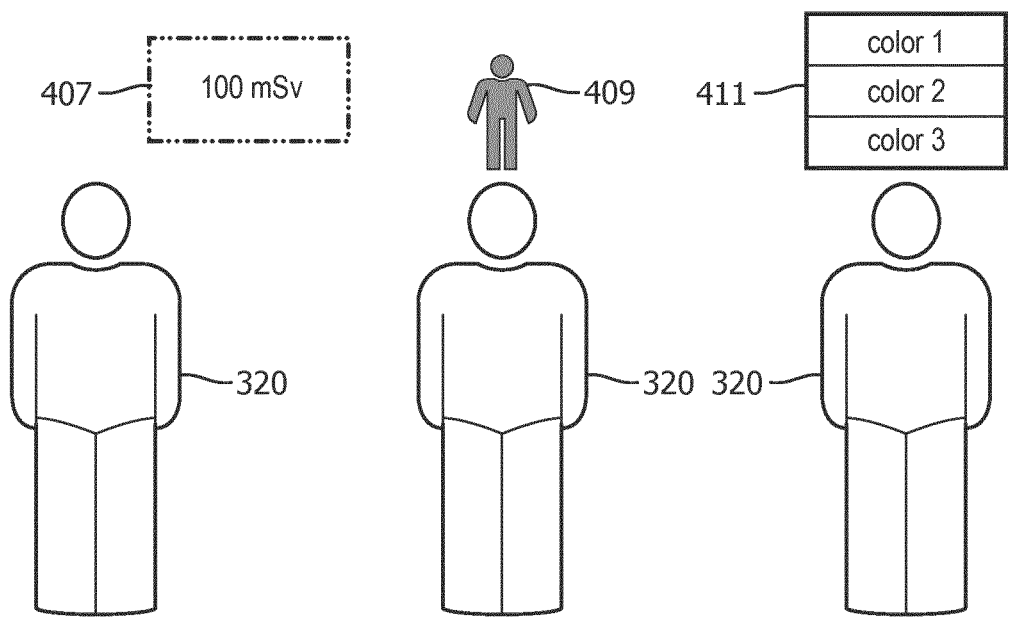
FIG. 4B is a diagram of medical personnel having a virtual object, such as an avatar or text or color indications associated therewith, in accordance with another embodiment.

FIG. 4B is a diagram of medical personnel having a virtual object, such as an avatar or text or color indications associated therewith, in accordance with another embodiment.

In another embodiment, a medical personnel 320 can have a virtual object that is represented by a text notification, or image notification, and/or color notification. For example, one user 320 can have text 407, e.g., "100 mSv" displayed in his/her vicinity. Such text 407 indicates the level of radiation that the user (leftmost) is exposed to during the medical procedure. The image/color notification can also be a real-time overlay of dose distribution to the medical personnel.

In another example, one user 320 (middle user) can have an "avatar" 409, such as a generic character. The avatar 409 can, e.g., change facial expressions as the radiations levels exposed to by the user 320 increase or decrease. The avatar 409 can also, e.g., gesture or speak as radiation levels are dynamically changing. In yet another example, one user (rightmost user) can have a color indication scheme or configuration 411, where different colors indicate different levels of radiation exposure. There could be a green zone, a yellow zone, and a red zone, where each zone is representative of different radiation level ranges that are acceptable, borderline, or unacceptable.

Therefore, the augmented reality system 350 (FIG. 3) comprises one or more sensors of a head-mounted augmented reality display system 329 to capture a set of data pertaining to a user of the head-mounted augmented reality display system, wherein a pose of the one or more sensors is known relative to the user, a processor 327 to calculate a set of parameters regarding a movement of the user 320 based at least in part on the captured set of data, and animating an avatar 409 based at least in part on the calculated set of parameters regarding the movement of the user, wherein the animated avatar is displayed as a virtual object when viewed through one or more augmented reality display systems.

In summary, the use of augmented reality can help to communicate the information about radiation in the OR. There are multiple ways in which this can be useful. One way is through the use dose avatars or dose virtual objects (FIGS. 4A and 4B). Each user's radiation badge 325 (FIG. 3) can be detected via a unique marker (e.g., a pattern, shape, QR code, color, etc.). A virtual object, such as an avatar can be associated with that radiation badge and can visually reflect the dose information. This can take on many forms. In one form, a sphere that changes color based on the instantaneous dose and that can grow in size with the cumulative dose. Alternatively, the sphere can change color based on cumulative dose and can grow/shrink in size with instantaneous dose. Instead of a sphere, a user-selected avatar that changes based on the dose information (e.g., an emoji that changes facial expressions from happy to sad with cumulative dose and that changes color along a grayscale to indicate instantaneous dose). Instead of a sphere or avatar, a set of numbers or text or color indications that float above the user's head or adjacent the user or in some vicinity of the user reflecting the radiation dose information can be introduced. Instead of the unique marker, each person in the room can be uniquely detected through facial recognition, recognition of the color of lead protection they are wearing, or through other camera-based recognition.

FIG. 5 is a block/flow diagram showing an operating room environment capable of displaying a radiation distribution map, in accordance with one embodiment.

The x-ray beams do not travel directly from the source to the detector. They scatter as they interact with various materials such as the table, the patient, instruments, etc. The scattered beams are what causes the majority of the dose to the staff in the room. Since the scattering events are complex, the staff in the room is often not aware of how much radiation they are receiving at any given time. If they are aware that they are receiving a lot of radiation then they can make subtle changes to their workflow (for example, a nurse shifting their position in the room slightly or an operator remembering to use a lower radiation level when the higher level is not clinically necessary).

In another embodiment, room radiation topology can be displayed to indicate regions within the OR with high levels, medium levels, and/or low levels of radiation exposure. The system can use any dosimeter readings that are present in the OR, combined with the geometry and radiation information from the c-arm, plus the camera view of the patient and room setup to model and then overlay on the view the distribution of radiation in the OR. The camera view can include 3D spatial mapping of the environment. The distribution of radiation in the OR can be shown in many ways, such as (i) small particles that exit the source and follow a trajectory, (ii) an overlay on any surfaces in the room that is color-coded by the amount of radiation encountering that surface, and (iii) an overlay of low-radiation locations to stand on (floor overlay, e.g., footprints) or below (ceiling overlay) to avoid radiation exposure. The location suggestions can be unique per staff member to avoid crowding, and minimize traffic, and distance travelled. This dose radiation system can be used to display cumulative historical information, current radiation, and expected radiation for upcoming x-ray use and this system could be used for training and simulation. The dose radiation system could alternatively be turned on occasionally during the procedure by the operator. The dose radiation system could be turned on when the c-arm gantry moves to a dramatically different position with a different expected radiation scatter distribution.

Referring to FIG. 5, the system 500 depicts an operating room (OR) 305 or medical environment 305 including an imaging device 310 that emits rays or beams or radiation 312. In one example, the imaging device 310 can be an x-ray device. The radiation 312 can be ionizing radiation. The radiation 312 is directed toward a patient 315 laying on a medical table 317. A plurality of medical personnel 320 can be working in the OR 305. The medical personnel 320 can include, for example, physicians, nurses, and other medical assistants. The medical personnel 320 can have a radiation dose measuring device 325 attached thereon. In one example, the radiation dose measuring device 325 can be a radiation dosimeter badge.

At least one medical personnel 320 can have a wearable electronic device 329. The wearable electronic device 329 can be, e.g., a head-mounted device 152 described in FIG. 1. The wearable electronic device 329 can include one or more processors 327. It is contemplated that one or more medical personnel 320 can wear a wearable electronic device 329. The electronic device 329 can receive at least geometry information 510, radiation information 520, and topology information 530. Processing of the information may be done by the electronic device's processor, or by a different workstation, or via cloud computing.

In operation, the imaging device 310 emits radiation 312 that scatters around the OR 305. The radiation distribution is shown by arrows 505. The radiation distribution 505 can be received by medical personnel 320, by the electronic device 329 worn by the medical personnel 329, by the medical equipment 330, by the displays 340, etc. In other words, the radiation distribution 505 is received by just about everyone and everything located within the OR 305.

The radiation distribution 505 can be mapped by a radiation distribution map 360. The radiation distribution map 360 can display various types of information. For example, surfaces or areas or regions of the OR 305 can be labeled as high exposure or low exposure sections. These sections can be discerned by using different color schemes. Red sections could designate high exposure areas, dark red areas can designated extremely dangerous levels of radiation, and thus send a notification, green areas can designate low exposure areas, dark green areas can designate very low or non-existent levels of radiation, etc. One skilled in the art can contemplate different color schemes indicating different levels of radiation.

The radiation distribution map 360 can also be customized for different personnel. For example, nurses can refer to a different radiation distribution map 360 than physicians. Other assistants who occasionally enter the OR 305 can also refer to a different radiation distribution map 360 generated or created specifically for them. Thus, each medical personnel 320 can have a different radiation distribution map 360 associated with him/her based on a number of factors/parameters (e.g., medical procedure performed, level of help needed, level of staff required, number of operations performed in other rooms, sterile/non-sterile staff, etc.).

Radiation distribution maps can be recorded and compared to future generated radiation distribution maps to determine how radiation levels change over a period of time. Prior radiation distribution maps can also be used to estimate radiation levels in future OR environments. Radiation distribution maps of one medical facility can be compared to distribution maps of other medical facilities. Such data can be collected and analyzed to determine, e.g., optimal medical room environment topology for different procedures, for different types of surgeons, for different type of geographical regions, etc. Radiation distribution maps can provide real-time feedback in the OR as an operation takes place. In other words, notifications or warnings can be sent to individuals detected within the OR to, e.g., move to a different location within the OR to realize less exposure to radiation. Thus, real-time feedback can be continuously received to dynamically update the radiation distribution maps.

Figure 6:
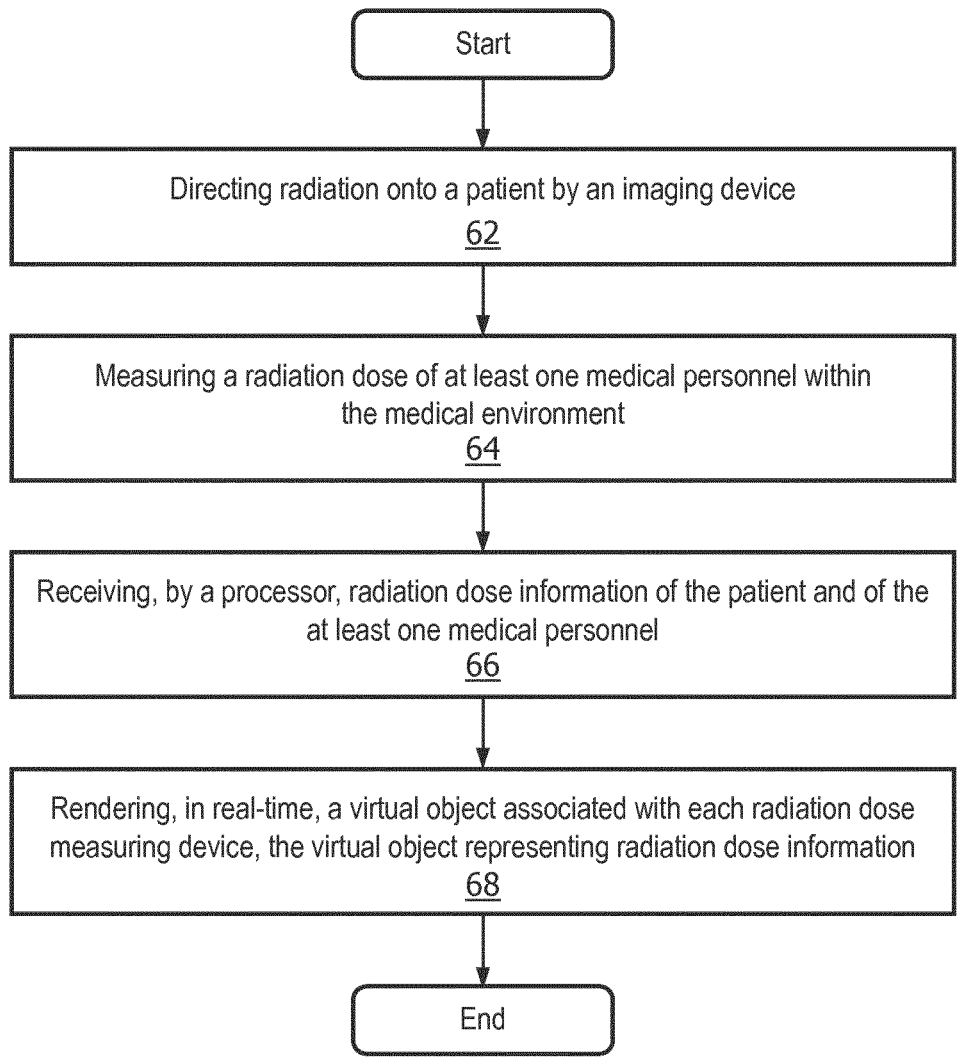
FIG. 6 is a flow diagram showing a method for monitoring radiation dose within in a medical environment in cooperation with augmented reality (AR) information, in accordance with illustrative embodiments.

FIG. 6 is a flow diagram showing a method for monitoring radiation dose within in a medical environment in cooperation with augmented reality (AR) information, in accordance with illustrative embodiments.

In block 62, radiation is directed onto a patient by an imaging device.

In block 64, a radiation dose of at least one medical personnel within the medical environment is measured by a radiation dose measuring device.

In block 66, radiation dose information of the patient or of the at least one medical personnel is received by a processor.

In block 68, a virtual object associated with each radiation dose measuring device is rendered in real-time, the virtual object representing radiation dose information.

Figure 7:
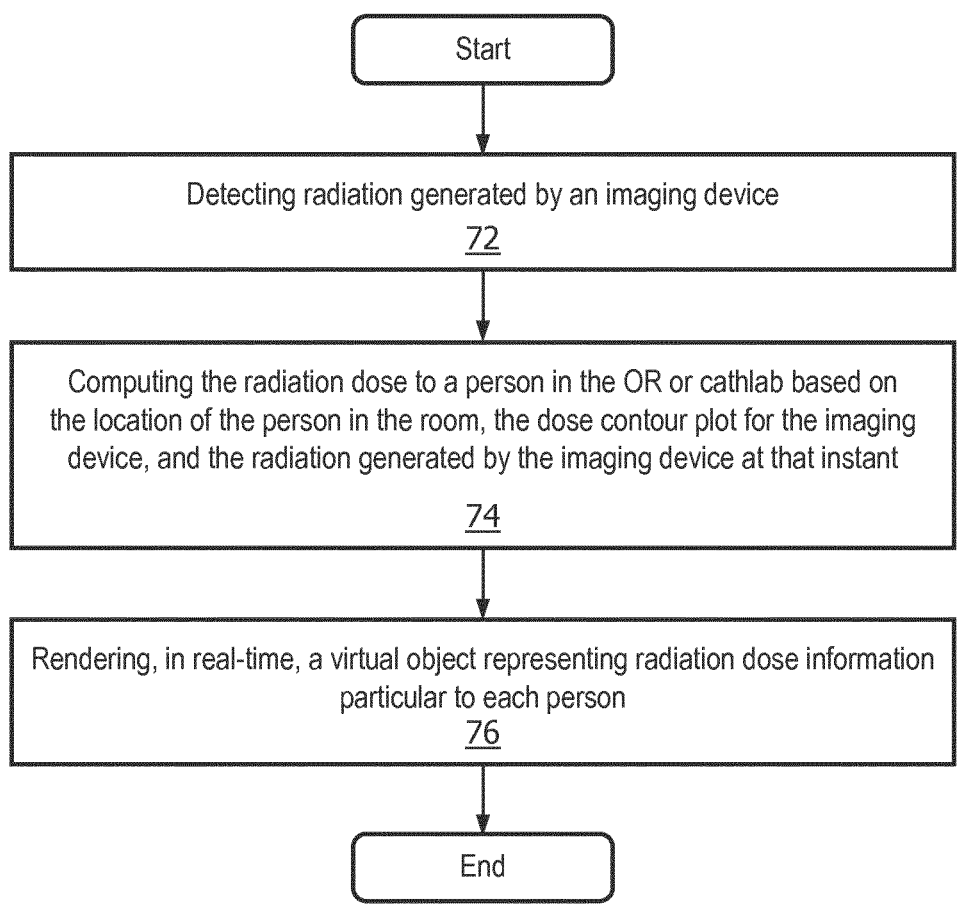
FIG. 7 is a flow diagram describing a method for computing the radiation dose within a medical environment in cooperation with augmented reality (AR) information, in accordance with illustrative embodiments, where the dose contour data is available with the imaging device (data is a contour plot of dose centered on the radiation source), where the position of the personnel is monitored with a camera looking at the room, and where the instantaneous radiation can be obtained from the imaging device, such that the instantaneous dose to the personnel can be computed.

FIG. 7 is a flow diagram describing a method for computing the radiation dose within a medical environment in cooperation with augmented reality (AR) information, in accordance with illustrative embodiments, where the dose contour data is available with the imaging device (data is a contour plot of dose centered on the radiation source), where the position of the personnel is monitored with a camera looking at the room, and where the instantaneous radiation can be obtained from the imaging device, such that the instantaneous dose to the personnel can be computed.

In block 72, detect the radiation generated by an imaging device.

In block 74, compute the radiation dose to a person in the OR or cathlab based on the location of the person in the room, the dose contour plot for the imaging device, and the radiation generated by the imaging device at that instant.

In block 76, render, in real-time, a virtual object representing radiation dose information particular to each person.

In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for augmented reality for radiation dose monitoring (which are intended to be illustrative and not limiting), it is noted that modifications and variations can be made by persons skilled in the art in light of the above teachings. It is therefore to be understood that changes may be made in the particular embodiments disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for radiation dose monitoring in a medical environment, the system comprising:
an imaging device configured to direct radiation onto a patient;
a radiation dose measurement device configured to measure a radiation dose of at least one medical personnel within the medical environment, wherein the radiation dose measurement device is configured to be attached to the at least one medical personnel; and
a processor configured to receive radiation dose information of the patient and of the at least one medical personnel, wherein the processor is configured to receive, from the imaging device, radiation information regarding the radiation emitted by the imaging device, and wherein the processor is configured to render, in real-time, a virtual object associated with the radiation dose measurement device, wherein the virtual object represents radiation dose information based on the radiation information received from the imaging device and the radiation dose information measured by the radiation dose measurement device.

2. The system as recited in claim 1, wherein the radiation dose measurement device is a dosimeter that includes a marker detectable by the processor.

3. The system as recited in claim 1, wherein the virtual object is an avatar that represents the radiation dose information.

4. The system as recited in claim 3, wherein the avatar is a sphere that transforms in size and color as the radiation dose information dynamically changes.

5. The system as recited in claim 3, wherein the avatar is selected by the at least one medical personnel associated with a respective radiation dose measurement device.

6. The system as recited in claim 3, wherein the avatar is one or more numbers or text that float adjacent the at least one medical personnel associated with a respective radiation dose measurement device.

7. The system as recited in claim 1, wherein the processor is incorporated in a wearable electronic device configured to be worn by the at least one medical personnel.

8. The system as recited in claim 1, wherein the radiation dose information of the patient or of the at least one medical personnel relates to instantaneous doses and cumulative doses.

9. The system as recited in claim 1, further comprising a radiation dose mapping device configured to map a radiation dose of the patient onto or in a vicinity of the patient, the radiation dose of the patient augmented with at least preoperative or intra-operative radiation information.

10. The system of claim 1, comprising a plurality of radiation dose measurement devices, wherein each of the plurality of radiation dose measurement devices is configured to be attached to a plurality of medical personnel, and wherein the processor is configured to generate a virtual object associated with each of the plurality of radiation dose measurement devices.

11. A system for radiation dose monitoring in a medical environment, the system comprising:
an imaging device configured to direct radiation onto a patient;
a radiation dose measurement device configured to measure a radiation dose of at least one medical personnel within the medical environment, wherein the radiation dose measurement device is configured to be attached to the at least one medical personnel;
a processor configured to receive at least:
radiation dose information of the patient and of the at least one medical personnel;
geometry information from the imaging device;
radiation information from the imaging device; and
topology information related to the medical environment; and
a display configured to render, in real-time, a virtual object associated with the radiation dose measurement device, wherein the virtual object represents radiation dose information based on the radiation information received from the imaging device and the radiation dose information measured by the radiation dose measurement device.

12. The system as recited in claim 11, wherein a distribution of radiation is represented as particles that are projected along one or more trajectories.

13. The system as recited in claim 11, wherein a distribution of radiation is represented as an overlay on one or more surfaces of the medical environment that are color-coded according to an amount of radiation encountered on each respective surface.

14. The system as recited in claim 11, wherein a distribution of radiation is represented as an overlay of low-radiation regions detected within the medical environment.

15. The system as recited in claim 11, wherein radiation proximity notifications are determined based on at least estimated radiation intensities to provide the at least one medical personnel with positive and negative radiation exposure regions within the medical environment before a medical procedure is performed on the patient.

16. The system as recited in claim 11, wherein the radiation dose measurement device is a dosimeter that includes a marker detectable by the processor, and wherein the processor is incorporated in a wearable electronic device configured to be worn by the at least one medical personnel within the medical environment.

17. The system of claim 11, comprising a plurality of radiation dose measurement devices, wherein each of the plurality of radiation dose measurement devices is configured to be attached to a plurality of medical personnel, and wherein the processor is configured to generate a virtual object associated with each of the plurality of radiation dose measurement devices.

18. A method for monitoring radiation dose in a medical environment, the method comprising:
- directing radiation onto a patient via an imaging device;
- measuring a radiation dose of at least one medical personnel within the medical environment via a radiation dose measuring device that is configured to be attached to the at least one medical personnel;
- receiving, by a processor, radiation dose information of the patient and of the at least one medical personnel;
- receiving, by the processor, radiation information regarding the radiation emitted by the imaging device; and
- rendering, in real-time, a virtual object associated with each radiation dose measuring device, the virtual object representing radiation dose information based on the radiation information received from the imaging device and the radiation dose information measured by the radiation dose measuring device.

19. The method as recited in claim 18, wherein the radiation dose measuring device is a dosimeter that includes a marker detectable by the processor.

20. The method as recited in claim 18, wherein the virtual object is an avatar representing radiation dose information.

21. The method as recited in claim 20, wherein the avatar is a sphere that transforms in size and color as the radiation dose information dynamically changes.

22. The method as recited in claim 20, wherein the avatar is selected by the at least one medical personnel associated with a respective radiation dose measuring device.

23. The method as recited in claim 20, wherein the avatar is one or more numbers or text that float adjacent the at least one medical personnel associated with a respective radiation dose measuring device.

24. The method as recited in claim 18, wherein the processor is incorporated in a wearable electronic device configured to be worn by the at least one medical personnel.

25. The method as recited in claim 18, wherein radiation dose information of the patient or the at least one medical personnel relates to instantaneous doses and cumulative doses.

26. The method as recited in claim 18, further comprising mapping, via a radiation dose mapping device, a radiation dose of the patient onto or in a vicinity of the patient, the radiation dose of the patient augmented with at least pre-operative or intra-operative radiation information.

27. The method of claim 18, comprising measuring a radiation dose of a plurality of medical personnel within the medical environment via a plurality of radiation dose measuring devices that are configured to be attached to each of the plurality of medical personnel, and generating a virtual object associated with each of the plurality of radiation dose measuring devices.

* * * * *